(12) United States Patent
Russell

(10) Patent No.: US 7,605,370 B2
(45) Date of Patent: Oct. 20, 2009

(54) MICROSPECTROMETER GAS ANALYZER

(75) Inventor: James T. Russell, Bellevue, WA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 11/648,851

(22) Filed: Dec. 29, 2006

(65) Prior Publication Data

US 2007/0164221 A1  Jul. 19, 2007

Related U.S. Application Data

(63) Continuation-in-part of application No. 10/939,279, filed on Sep. 10, 2004, now Pat. No. 7,157,711, which is a continuation-in-part of application No. 10/227,135, filed on Aug. 23, 2002, now Pat. No. 6,791,086.

(60) Provisional application No. 60/316,763, filed on Aug. 31, 2001.

(51) Int. Cl.
    *G01J 3/18* (2006.01)
(52) U.S. Cl. .................. 250/339.07; 250/351; 250/353; 356/305; 356/328
(58) Field of Classification Search ............ 250/339.07, 250/351, 353; 356/305, 328
    See application file for complete search history.

(56) References Cited

U.S. PATENT DOCUMENTS

| | | | |
|---|---|---|---|
| 4,060,327 A | 11/1977 | Jacobowitz et al. | |
| 4,320,971 A | 3/1982 | Hashimoto et al. | |
| 4,961,646 A | 10/1990 | Schrammli et al. | |
| 4,997,281 A * | 3/1991 | Stark | 356/328 |
| 5,451,787 A | 9/1995 | Taylor | |
| 5,731,874 A | 3/1998 | Maluf | |
| 5,801,826 A | 9/1998 | Williams | |
| 5,807,750 A | 9/1998 | Baum et al. | |
| 5,880,834 A | 3/1999 | Chrisp | |
| 5,905,571 A | 5/1999 | Butler et al. | |
| 5,931,161 A | 8/1999 | Keilbach et al. | |
| 5,999,319 A | 12/1999 | Castrancane | |
| 6,039,697 A | 3/2000 | Wilke et al. | |
| 6,201,629 B1 | 3/2001 | McClelland et al. | |
| 6,249,346 B1 | 6/2001 | Chen et al. | |
| 6,791,086 B2 | 9/2004 | Russell | |
| 2005/0057750 A1 * | 3/2005 | Schenk et al. | 356/328 |

FOREIGN PATENT DOCUMENTS

EP   0 271 602   6/1988

OTHER PUBLICATIONS

Supplementary European Search Report, Dec. 27, 2007.

* cited by examiner

*Primary Examiner*—David P Porta
*Assistant Examiner*—Shun Lee

(57) ABSTRACT

A robust, compact spectrometer apparatus for determining respective concentrations or partial pressures of multiple gases in a gas sample with single as well as multiple and even overlapping, absorption or emission spectra that span a wide spectral range.

5 Claims, 11 Drawing Sheets

MICROSPECTROMETER GAS ANALYZER

CROSS-REFERENCE TO RELATED APPLICATIONS

This application claims priority under 35 U.S.C. §120 as a Continuation-In-Part (CIP) from U.S. patent application Ser. No. 10/939,279, filed Sep. 10, 2004, now U.S. Pat. No. 7,157,711, which claims priority under 35 U.S.C. §120 as a CIP from U.S. patent application Ser. No. 10/227,135, filed Aug. 23, 2002, now U.S. Pat. No. 6,791,086, which claims priority from U.S. Provisional Application Ser. No. 60/316,763, filed Aug. 31, 2001 under the provisions of 35 U.S.C. §119(e), the contents of each of which are hereby incorporated by reference in their entirety.

BACKGROUND OF THE INVENTION

1. Field of the Invention

This invention relates to a method and apparatus for efficiently and robustly measuring gas concentrations/partial pressure of respiratory and anesthetic gases.

2. Description of the Related Art

It is well known by those of ordinary skill in the art that gas analyzers of the nondispersive infrared (NDIR) type operate on the principle that the concentration of specific gases can be determined by (a) directing infrared radiation (IR) through a sample of a gaseous mixture, (b) separately filtering this infrared radiation to minimize the energy outside the band absorbed by each specific gas (c) measuring the filtered radiation impinging upon one or more detecting devices and (d) relating a measure of the infrared absorption of each gas to its concentration. Gases that may be measured exhibit increased absorption (and reduced transmittance) at specific wavelengths in the infrared spectrum such that, the greater the gas concentration, the proportionally greater absorption and lower transmittance. An extension of this NDIR technique uses a continuous, linear bandpass filter, followed by a linear array of detectors.

Gas analyzers are widely used in medical applications and may be characterized as being located either in the main path of the patient's respiratory gases (mainstream analyzers) or in an ancillary path usually paralleling the main path (sidestream analyzers). A mainstream analyzer is situated such that the subject's inspired and expired respiratory gases pass through an airway adapter onto which the analyzer is placed. Mainstream designs require the optical and electronic components to be interfaced to a patient's airway or to a respiratory circuit in communication with a patient in a location in relatively close proximity to the patient. As a result, to be accepted in clinical use, the mainstream gas analyzer must be designed as a compact, lightweight yet robust structure unaffected by typical mechanical abuse and temperature variations associated with prolonged use in health care facilities.

While conventional mainstream gas analyzers work well for a small number of specific, non-overlapping spectrum wavelengths, it is difficult to change wavelengths of interest. The system becomes increasingly inefficient if there are more than 2 or 3 wavelengths of interest, and it is very difficult and expensive to provide resolutions significantly better than 0.1 micron, FWHM (full-width at half maximum) in the IR region.

It is known to use grating spectrometers for gas analysis. There are two general configurations of grating spectrometers: the spectrograph, which originally spreads the spectrum out over a strip of photographic film or a linear array detector, and the spectrometer, which uses a single detector that is set at an appropriate location or angle to register a particular spectral element.

For IR gas measurements, an IR source provides broadband energy that is collimated and passed through a gas sample cell. The collimated broadband energy, now attenuated at certain wavelengths, is directed to a diffraction grating where it is diffracted from the grating, spread out into a continuous spectrum, and focused with a mirror onto a small detector. The diffraction grating is rotated about an axis parallel to the grating lines, and substantially coaxial with the face of the diffraction grating. As the diffraction grating is rotated, the spectrum is scanned past the single detector. Since the diffraction grating rotation is synchronized with the detector readout electronics, specific, but arbitrary, spectrum features can be isolated and registered.

It is axiomatic that a microspectrometer should be small and lightweight. The present invention contemplates, for example, that the microspectrometer is made small and lightweight enough to be used directly on a patient airway, i.e., mounted in a mainstream fashion on a patient circuit. While the optics can, in general, be made small enough to suit the purpose, it is difficult to make the mechanism that drives the diffraction grating, that is, the spectrum scanner, sufficiently small to suit this purpose. Currently available electro-mechanical scanner drives that are much too large, mostly too heavy, require too much power, and cost too much to be used in this manner.

For example, many conventional spectrometers rotate the diffraction grating using a motor of some sort, oscillating linkages to drive the diffraction grating from the motor, and a bearing assembly. While such an arrangement can deliver good results, such a structure is relatively large, heavy and expensive. Other conventional spectrometers use an oscillating motor, sometimes called a galvanometer drive, in place of the motor and linkage. Such arrangements are less expensive, but still large, heavy and relatively expensive.

U.S. Pat. Nos. 6,249,346 (2001) to Chen, et al., 6,039,697 (2000) to Wilke, et al., and 5,931,161 (1999) to Keilbach, et al. all disclose relatively smaller sized spectrometers, but of designs that are of undue bulk and, in some instances, complexity.

SUMMARY OF THE INVENTION

Accordingly, it is an object of the present invention to provide a spectrometer that overcomes the shortcomings of conventional gas analyzing devices. This object is achieved according to one embodiment of the present invention by providing a robust spectrometer apparatus for determining respective concentrations or partial pressures of multiple gases in a gas sample with single, as well as multiple and even overlapping, absorption, or emission spectra that span a wide spectral range.

The present invention adapts a grating spectrometer for use in a compact respiratory gas analysis instrument. Specifically, the present invention employs a scanning spectrometer, which scans, or sweeps, the spectrum across a fixed detector. From an optical point of view, this apparatus may be characterized as a modified Ebert scanning monochrometer.

A very small, inexpensive oscillating mirror may be made using a MEMS (MicroElectroMechanical System) fabrication process. With a diffraction grating added to the mirror surface, this structure provides a very low cost, small, lightweight but rugged scanner for an in-line IR gas analysis instrument.

Spectrum resolution is primarily a function of the grating size, aperture, line pitch, diffraction order, and collimation. In the present invention, the required grating width is in the 1 to 2 mm range, which is well suited to existing MEMS technology. The other parameters are easily obtained or controlled, at least well enough for necessary accuracy.

The diffraction grating may be formed separately and glued on to the "mirror" surface or, preferentially, the diffraction grating may be formed in the surface of the mirror as part of the MEMS fabrication processing. A hologram type of grating may also be used. The drive to make the mirror oscillate may be magnetic, wherein the mirror either has a planar coil formed on the back or the mirror itself is made magnetic or, alternatively, the mirror may be driven electrostatically. Because the required angular amplitude is relatively small, an electrostatic drive is currently preferred.

The apparatus of the present invention may also be configured in several additional ways. In one instance, the oscillating grating may be removed and replaced by a scanning (oscillating) mirror. In an embodiment of this approach, the mirror scans the input light over a fixed grating, which disperses the spectrum. As before, the spectrum is focused by a mirror onto the detector plane. While this alternative method requires one additional component, the manufacturing cost may be less because the MEMS oscillating element does not need to have a grating fabricated on its surface.

In yet another alternative embodiment, the oscillating mirror may be positioned to direct the attenuated broadband energy beam back through the gas sample cell, with the grating and detector on the same side of the gas sample cell as the IR source. The advantage of this arrangement is higher sensitivity (due to the double pass through the gas in the cell), and a somewhat narrower package. Alternatively, in the double pass configuration, the mirror on the side opposite to the source may be fixed, and an oscillating mirror/fixed grating (or oscillating grating) and detector system located on the source side. These various embodiments may be configured in a single plane or the oscillating mirror, scanning grating or a focusing mirror may be rotated in orientation to direct the beam in a different plane, so that different package configurations may be easily accommodated.

A diffraction grating can provide diffracted beams in several orders. Ordinarily, the first order is used, either + or −1, and the shape of the grooves in the grating are designed to emphasize the chosen order. However, there can be some residual energy in higher orders. The result is that spectral regions at a shorter wavelength may overlap the first order spectrum. This problem may be solved, as required, with a blocking filter set to cut off all wavelengths that are outside of a spectral region of interest.

Data processing electronics for the apparatus of the present invention are synchronized with the motion of the scanning element. One approach is to extract a timing signal from the mirror drive. Alternatively, the mirror may have coils or magnetic or piezoelectric sensors mounted on it to provide signals indicative of a substantially instantaneous location of a portion of the mirror for use in synchronization. Another sensing technique for using in synchronization is to reflect an auxiliary beam off the front or back of the mirror to a separate detector. A currently preferred technique is to use a unique feature of the detected spectrum, if such is available or provided. Assuming that the mirror is resonant, there will be relatively long periods when the detector will not receive any signal. This is because the scan will be more easily interpreted if it is in the more nearly linear part of the scan, and because the blocking filter will remove all signals prior to, or following, the spectral region of interest. As such, the long blank period followed by a sharp rise in signal may be used to provide a suitably unique marker to a phase lock loop synchronizer. The blank period also provides a background light condition so that the detector zero may be set. Full scale can be implied by any spectral region between absorption peaks, or regions where known peaks have been subtracted.

Note that because the data generated by the apparatus is continuous, it is believed to be possible to incrementally subtract known, and previously stored, specific spectral lines, i.e., "peel off" individual lines, one by one. Such processing improves separation, or reduces interference, especially of weak lines.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1A:
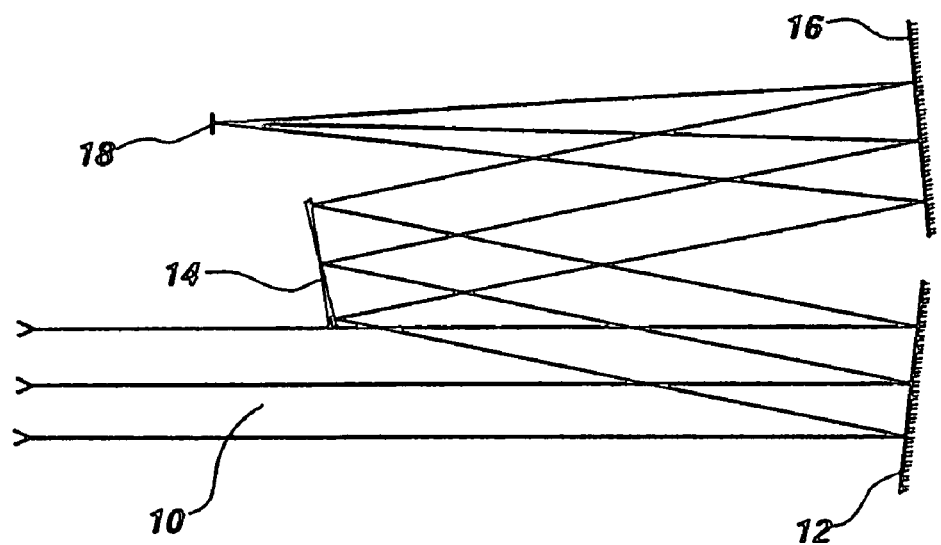
FIG. 1A is a schematic optical system layout for a spectrometer with an oscillating scanner mirror-diffraction grating combination according to the principles of the present invention.

FIG. 1A is a schematic optical layout for a spectrometer according to the principles of the present invention. Energy in the form of a light beam 10, such as an infrared beam, proceeds from a sample cell G (see FIG. 1B) and strikes a turning mirror 12. Turning mirror 12 then reflects light beam 10 towards scanning grating reflector 14, which may also be termed a scanning mirror. It should be noted that scanning grating reflector 14 oscillates about an axis perpendicular to the page (the oscillations are shown in an exaggerated form). From the scanning grating reflector 14, the now-dispersed light beam 10 travels to a focusing mirror 16 which, in turn, focuses light beam 10 to the detector 18 which includes, or has associated therewith, appropriate readout circuitry. Detector 18 may comprise, for example, a slit- or pinhole-defined detector, as known in the art.

Figure 1B:
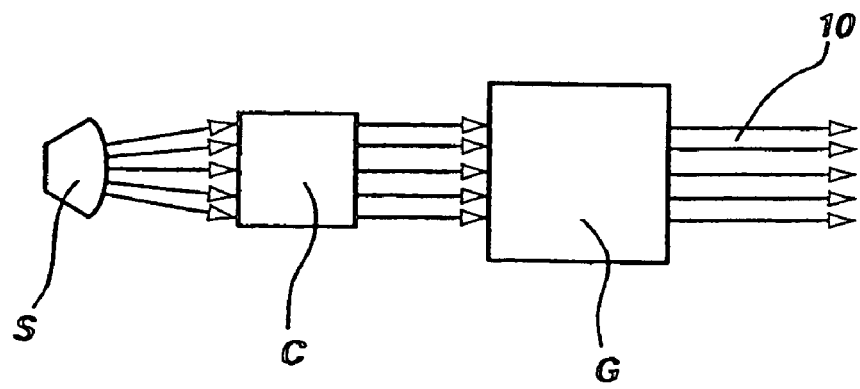
FIG. 1B is a schematic diagram of the spectrometer in which the optical system of FIG. 1A can be suitably employed.

FIG. 1B schematically illustrates the complete the structure of a spectrometer for use with the various optical embodiments of the present invention. As shown in FIG. 1B, an infrared light source S emits an infrared beam which may be collimated using source optics or a collimator C, as shown. The collimated infrared beam then enters gas sample cell G, exiting same to turning mirror 12. Such an arrangement may be used with all of the described embodiments herein, except it is notable that the embodiments of FIGS. 5A through 5C do not require the presence of a collimator C or source optics to collimate the infrared beam.

Figure 2:
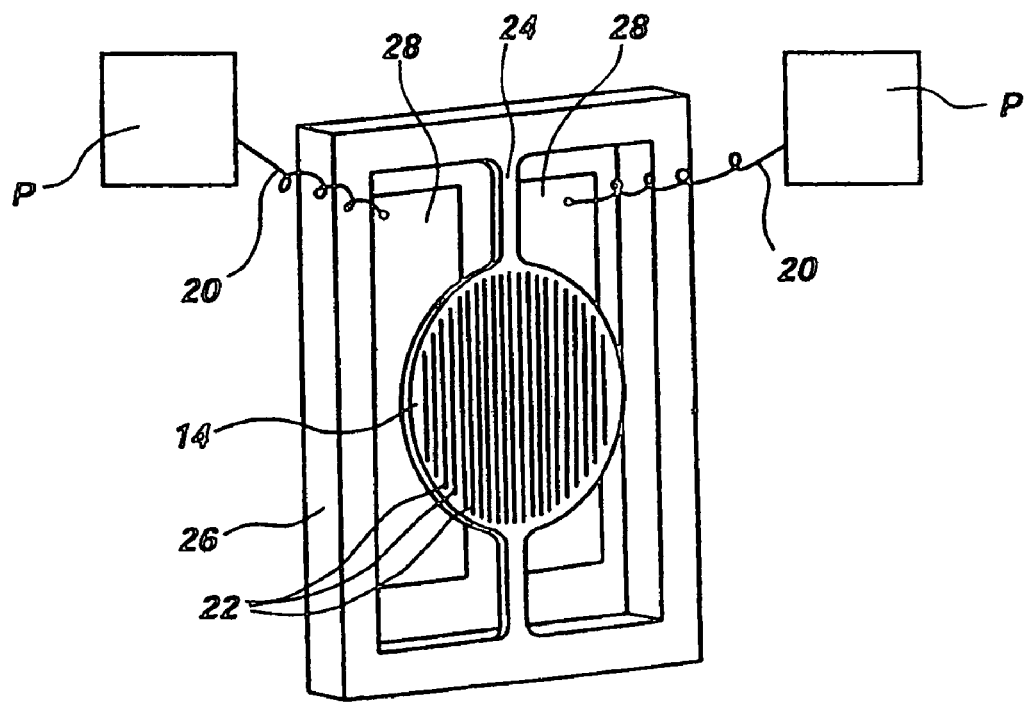
FIG. 2 is a perspective view of an oscillating mirror/grating combination suitable for use in the optical system of FIG. 1A.

Referring to FIG. 2, scanning grating reflector 14 has diffraction grating lines 22 positioned on it. The lines may be glued on or machined into the reflective, mirror surface using a MEMS process, or they may be positioned through some other known technique. U.S. Pat. No. 6,201,269 to McClelland, et al., the disclosure of which is incorporated herein by reference, discloses a suitable MEMS process for fabricating an oscillating mirror, which process may be adapted to fabricate scanning grating reflector 14. The grating can also be made in the form of a hologram.

Scanning grating reflector 14 has a flexure axis 24 parallel to diffraction lines 22 and is mounted to a frame 26 through support members coaxial with flexure axis 24. Backings 28 may be electrically conductive so as to provide an electrostatic drive for scanning grating reflector 14 when leads 20 are connected between backing 28 and a suitable power source P as known in the art. Two power sources P are depicted for simplicity in FIG. 2 although, of course, a single power source P may be used to power backings 28 in alternation.

Figure 3:
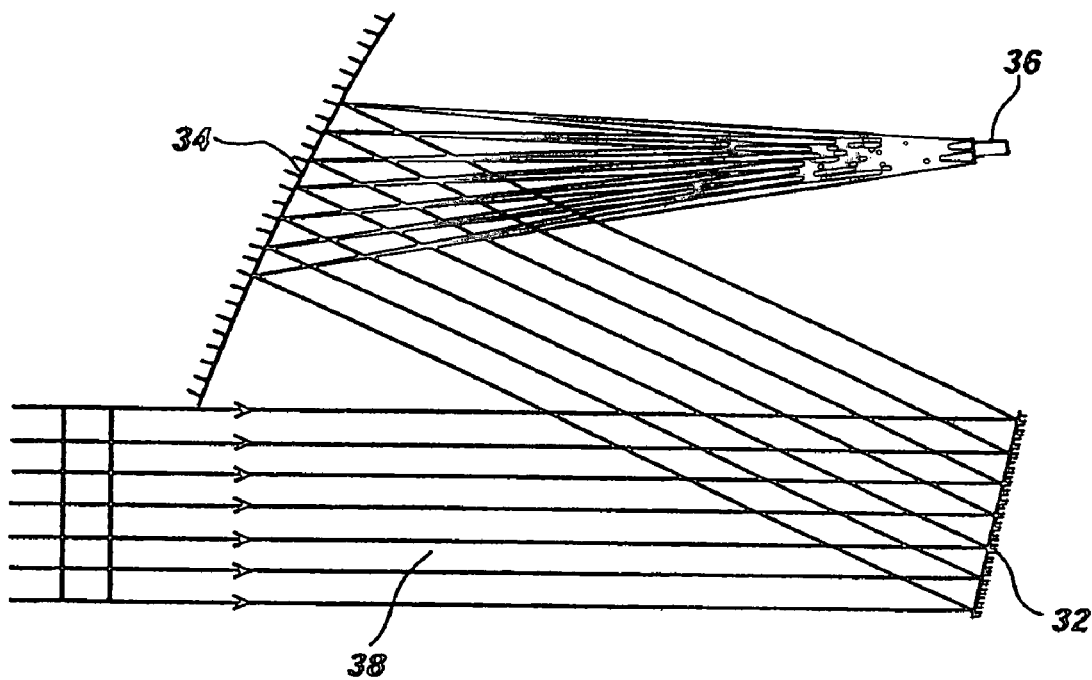
FIG. 3 is a schematic optical system layout for a spectrometer with a focusing mirror-diffraction grating combination according to the present invention.

The schematic illustrated in FIG. 1A uses scanning grating reflector 14 as both scanner and diffraction grating. However, it is not necessary to include the diffraction grating on the scanner. The diffraction grating may be scanned in angle by a mirror scanner instead. As shown in FIG. 3, a mirror scanner 32 is used to sweep the input beam 38 from the gas sample cell over the diffraction grating and mirror combination 34. The mirror employed in diffraction grating and mirror combination 34 is a focusing element that directs and focuses dispersed energy from mirror scanner 32 to the detector 36. The image formed is of the defining input aperture, in the wavelength selected by the diffraction grating and mirror combination 34. In a conventional Ebert monochromator, there is a slit at the entrance to the monochrometer that defines the aperture to be imaged. In the present invention, the defining aperture may be the source, or it may be a separate aperture near the entrance to the scanner/detector assembly. It should be noted that the turning mirror 12 of the embodiment of FIG. 1A does not have a structural counterpart in FIG. 3, as the turning mirror is not a required component of the invention, but is common in the prior art and use thereof does provide a number of other configuration possibilities.

As another alternative configuration, the mirror-grating function may be split up, such that the scan is directed to a flat grating mirror, followed by a focusing element, usually a mirror in this IR wavelength region, followed by the detector. The advantage of such alternative split configuration over the FIG. 1A configuration is that the scanning mirror device is directly manufacturable by presently known processes, while forming a grating on the mirror is not conventional. In contrast, forming a grating on a focusing element by molding techniques is conventional. The disadvantages of the split configuration are that the grating must be somewhat larger (because the beam moves across the grating in order to change the angle), and the mirror may need to be an asphere. These are minor issues if, as expected, the grating-mirror is made by a molding or casting process.

The embodiments described with respect to FIGS. 1A and 3 provide an effective way to collect spectral data over a wavelength octave. However, these embodiments are designed with a single band, such as, for example, the 3 to 5 micron band, in mind.

The range of a grating spectrometer is limited in a practical sense to an octave, because of multiple orders. That is, a particular wavelength will diffract at a certain set of angles, which depend on the wavelength, the grating period, and an integral number known as the Order. Because the dispersion is a function of the Order, multiple orders can overlap at the detector plane, making spectra difficult to interpret. In practical grating spectrometers, the grating is made so that most of the diffracted energy is directed to a particular desired order. This is done by contouring the surface at each groove of the diffraction grating so that light striking that point will be reflected in the same direction as the desired diffraction order. This contouring process is referred to as blazing. In addition, blocking filters may be added at the spectrometer input or at the detector that will block wavelength regions that might otherwise cause confusion.

In addition to the 3 to 5 micron band described earlier, it is advantageous for the present invention to measure the 7 to 10 micron range simultaneously. The problems in this longer wavelength range are that, first, a more expensive detector is required, second, transmission optics, e.g., lenses, for beam manipulation tend to be more expensive (although a long-wave pass filter or function is unavoidable) and third, the second order of the 3 to 5 micron band would tend to fall in the same plane as the 7 to 10 micron band.

Seven exemplary approaches to optical arrangements for the measurement of additional bands are shown in FIGS. 4A-4F. Note that in all illustrated embodiments shown in FIG. 4A-4F, the input beam has already been collimated, either by the source optics, or by other conventional means. Note also that the drawings are schematic, i.e., the diffraction angles are illustrative and not exact.

Figure 4A:
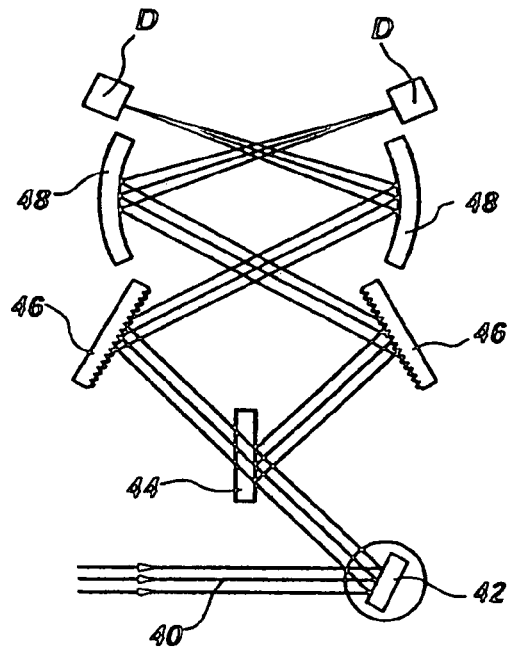
FIGS. 4A through 4F are schematic illustrations of a number of exemplary layouts for spectrometers using collimated light beams, enabling analysis of a plurality of spectral bands in accordance with the principles of the present invention.

In the embodiment of FIG. 4A, a scanning mirror 42 directs the input beam 40 to a dichroic beam splitter 44, which divides the beam into two bands, e.g., 3 to 5 and 7 to 10 microns, respectively. Two separate scanning diffraction gratings 46 disperse the bands; each grating 46 being optimized for a respective band. After dispersion, each band of the beam is directed by a focusing mirror 48 onto an aperture of a detector D.

Figure 4B:
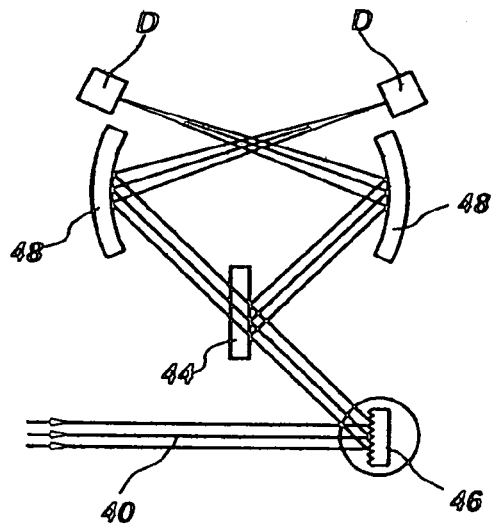

In the embodiment of FIG. 4B, a scanning diffraction grating 46 is employed, and the resultant dispersed beam is divided by a dichroic beam splitter 44 into two bands. In this case, the scanning diffraction grating 46 has been optimized for the 7-10 micron band in first order, and also for the 3-5 micron band in second order.

Figure 4C:
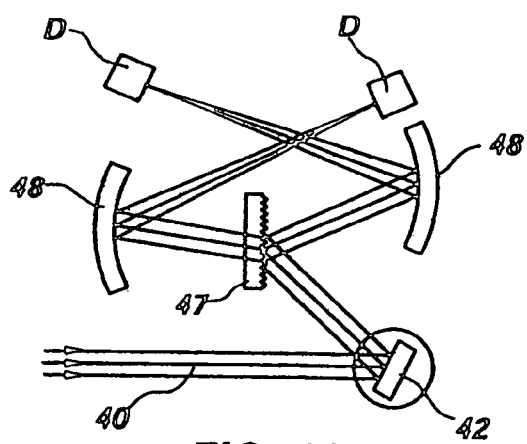

FIG. 4C illustrates an embodiment including a scanning mirror 42, followed by a dichroic diffraction grating 47 that is coated to reflect one band, such as 7-10 microns, and transmit the other. As in other cases, the dichroic diffraction grating 47 would be arranged for first order 7-10 microns, and second order 3-5 microns. Alternatively, a reflective diffraction grating (non-transmissive) may be employed, and a band splitter located after the diffraction grating.

Figure 4D:
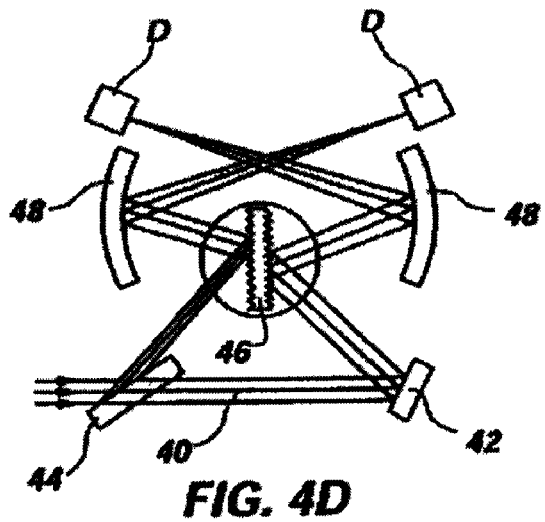

The embodiment of FIG. 4D uses back-to-back scanning diffraction gratings 46 that only reflect, and together are used as the scanning element. Band splitting is effected by a dichroic beam splitter 44 before the gratings. In this embodiment the gratings may be individually optimized for best performance in specific bands.

Figure 4E:
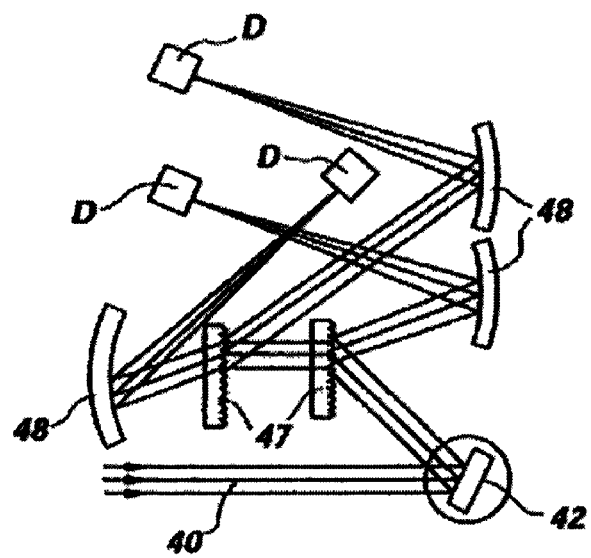

The embodiment of FIG. 4E is arranged to provide detection in three bands. The scanning mirror 42 illuminates two reflection/transmission dichroic diffraction gratings 47 in series. While this arrangement causes some restrictions on wavelength band placement, it is physically more compact than that of FIG. 4F.

Figure 4F:
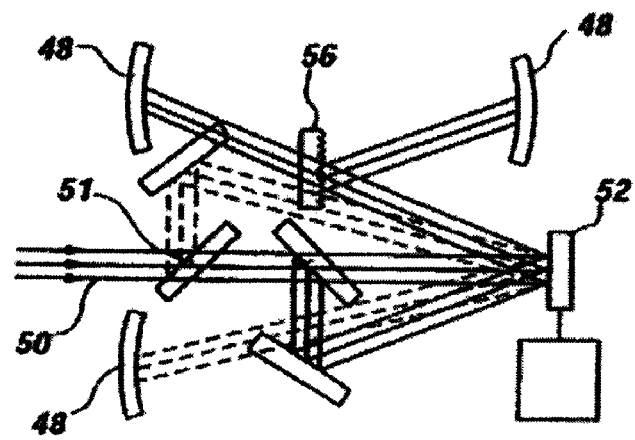

The embodiment of FIG. 4F includes a three-dimensional arrangement of mirrors and gratings that can provide six bands (as shown), and more bands by extension. The input beam 50 is first split into three wavelength blocks of two contiguous octave bands each using multiple dichroic or bandpass filters 51, which wavelength blocks are then scanned by a scanning mirror 52. The axis of the scanning mirror 52 is in the plane of the drawing sheet. The wavelength blocks are geometrically separated by angle in a plane that includes the mirror rotation axis. After scanning, the wavelength blocks go to three diffraction gratings 56, each similar to that FIG. 4C but suitably tilted to match the separation angle. Note that only one grating 56, and no detectors, are shown for simplicity and clarity of illustration in FIG. 4F, although such would be included in practice.

Figure 5A:
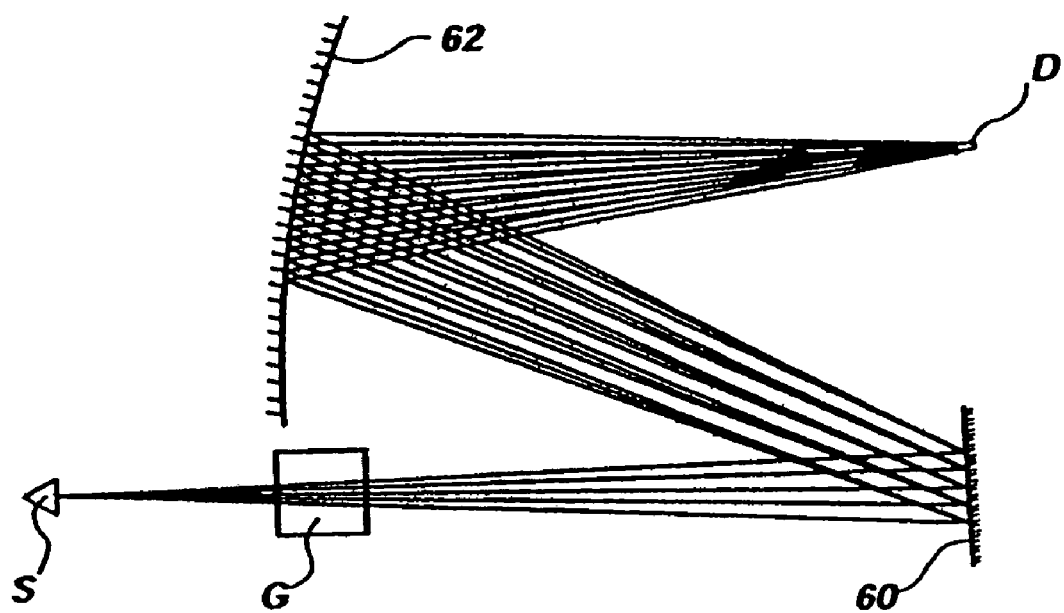
FIGS. 5A through 5C are schematic illustrations of a number of exemplary layouts for spectrometers using non-collimated light beams, enabling analysis of a plurality of spectral bands in accordance with the principles of the present invention.
Figure 5B:
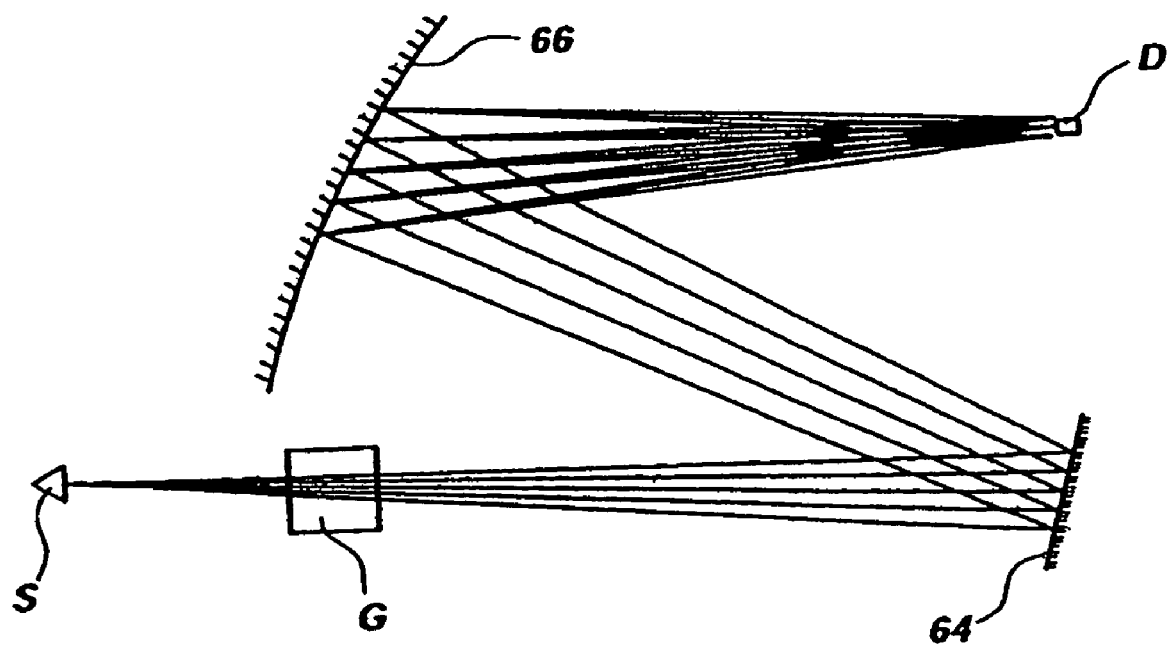
Figure 5C:
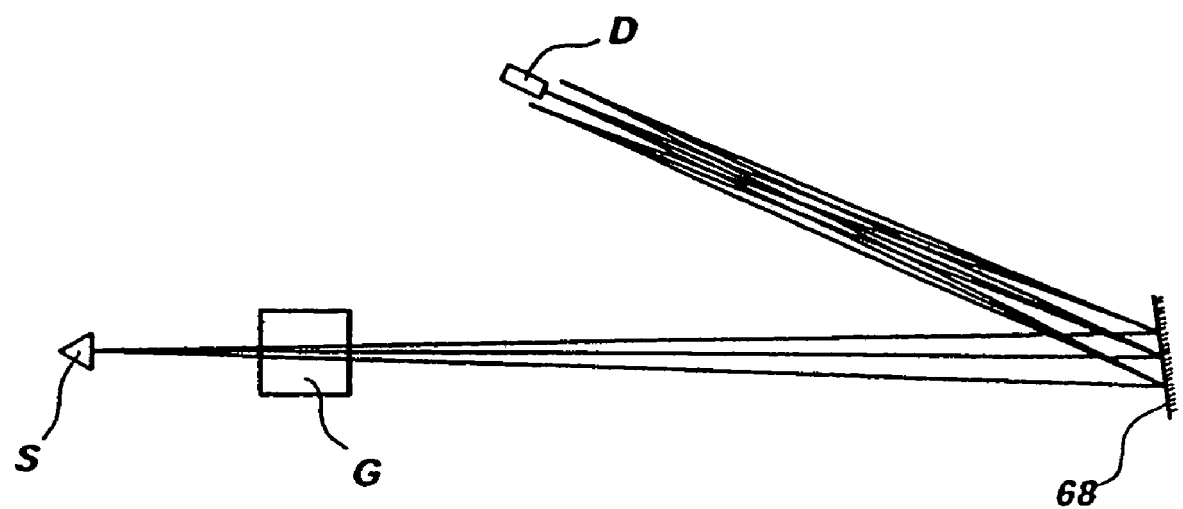

FIGS. 5A-5C depict additional embodiments of the present invention wherein, unlike those described above, light entering the spectrometer may be diverging or converging and the optics modified to compensate therefore.

FIG. 5A schematically depicts a system wherein light from a source S passes through gas sample cell G and is reflected, dispersed by a grating and scanned on a scanning flat grating mirror 60. The resultant dispersed light beam is focused using a concave mirror 62 onto detector D.

FIG. 5B schematically depicts a system using a flat scanning mirror 64, and the scanned beam is reflected to a concave grating mirror 66 that diffracts and focuses the light beam onto detector D.

FIG. 5C schematically depicts a system wherein the scanning, dispersion and focusing functions are consolidated into a single element 68 in the form of a scanning mirror which includes a diffraction grating and is concave for focusing the light beam onto detector D.

As will be understood and appreciated by those of ordinary skill in the art, adding functions to a scanning element increases the cost thereof, but in each instance other elements in a system may be reduced in cost, or eliminated entirely. In particular, the embodiments of FIGS. 5A-5C eliminate the need for collimating elements, and the embodiment of FIG. 5C eliminates the need for a separate focusing mirror. Such reductions in the number of required components enable the fabrication of a less costly system due both to elimination of components and a reduction in assembly time.

It will also be understood and appreciated by those of ordinary skill in the art, the approaches illustrated in FIGS. 5A-5C may be applied to the embodiments of FIGS. 4A-4F for the measurement of multiple bands of interest. For example, the components and arrangement of FIG. 5A may be advantageously employed to modify the systems of FIGS. 4B and 4D, while the components and arrangement of FIG. 5B may be advantageously employed to modify the system of FIG. 4A, in each instance resulting in the elimination of a focusing mirror. The components and arrangement of FIG. 5B may also be employed in the systems of FIGS. 4C, 4E and 4F, although the focusing mirror and grating element would be more complex, since it would be required to focus in both reflection and transmission. The first, or reflecting, face would be concave, while the second face would comprise a convex refracting face.

In the embodiments described above, two different bands, i.e., the 3.5-4.5 micron and 7-9 micron bands, are separately dispersed using the first and second Orders of the grating. Filters on the two detectors make sure that the respective detectors only react to the proper band. The present invention also contemplates using different Orders of the grating provide for (essentially) non-contiguous bands that cover a much larger range of wavelengths than could be obtained by a single order grating.

The invention described above also discloses the use of a dichroic splitter to direct different bands or segments of a band to two different detectors to the detector(s). The present invention also contemplates using a non-wavelength sensitive splitter, i.e., an ordinary partially reflective splitter. In which case, appropriate filters can be provided on or before the detectors to sort out the proper bands.

The above-described embodiments of the present invention use a focusing mirror to form an image at the detector. This focusing function could also be performed with a lens formed from any suitable material. The present invention further contemplates that the dichroic splitter can be a partially reflective splitter. In addition, the splitter (reflective or transmissive) can be disposed after the focusing mirror (or lens), and before the two detectors.

One function of the microspectrometer of the present invention is to perform a spectral scan of anesthetic agents in the 8 to 10 micron IR band, and concurrently, a scan of the mid-IR $CO_2$ and $N_2O$ band. The selection of a basic structure for a spectrometer is easy, due to the existence of numerous historical systems, e.g., Ebert, Czerny-Terner, Fastie-Ebert, etc, and single or multiple holographic grating systems. The primary system problem is efficiency, that is, how much of the source light can be deposited on the detector vs. the spectral resolution of the system.

In all systems, the source, or an aperture illuminated by the source, is imaged onto the sensor plane. The size of this image, set by aberrations and optical magnification, must be less than the desired spectral resolution of the system. Because the resolution is set by the grating, the effective source size is critical. In a typical spectrometer system, the entrance slit is at the focus of a large aperture mirror. The mirror collimates the light onto a grating. Diffracted light from the grating is refocused onto the sensor by a second concave mirror. Because the aperture is large, i.e., a small f number, the efficiency can be large. In the microspectrometer of the present invention, light from the source must first pass through the airway adapter (sample cell) that, in the absence of added optics, would prevent a large aperture/high efficiency system. Even if the beam from the source were to be collimated through the adapter, the source size would make the beam spread too large for practical optics in the spectrometer.

As shown in FIGS. 6A-6D, the present invention solves this problem through the use of a large aperture lens at the source that forms an aerial image in the middle of the adapter, i.e., sample cell. A lens 103 at the entrance to the detector block will roughly collimate that light directly on to a grating. Lens 103 has a focal length that is about equal to the image distance of the lens proximate to the source. Lens 103 collimates the beam, and because it is working from an image of the source, lens 103 tends to collimate the angle of the off-axis beams. The action is similar to that of a field lens. Therefore, the beam spread at the grating is less, and very much less at the following elements.

Figure 6A:
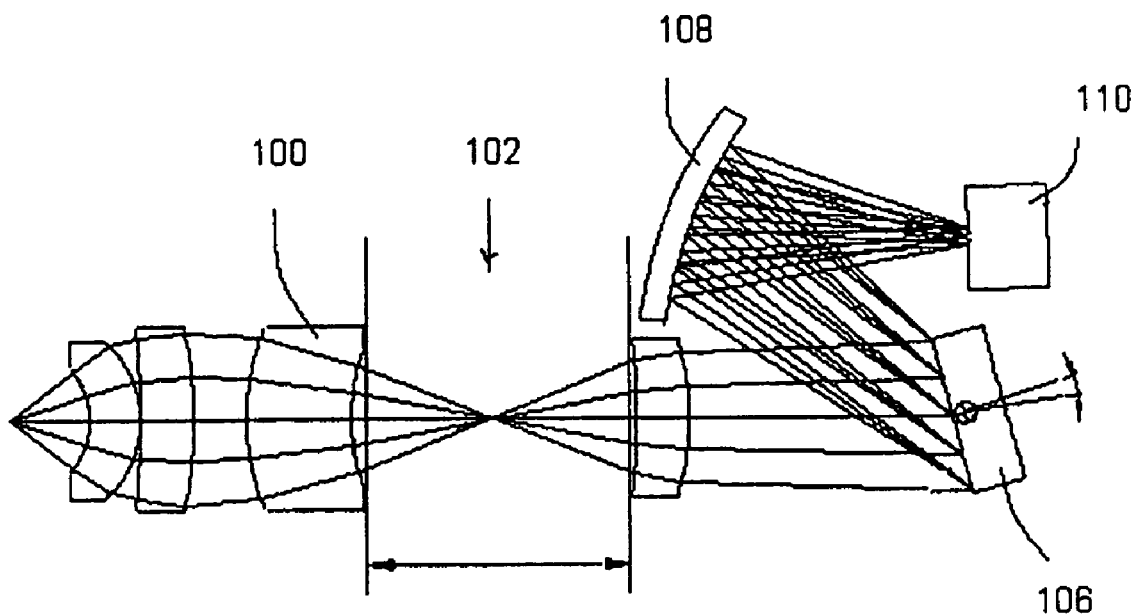
FIGS. 6A-6D are schematic illustrations of further exemplary arrangements for the spectrometers in accordance with the principles of the present invention
Figure 6B:
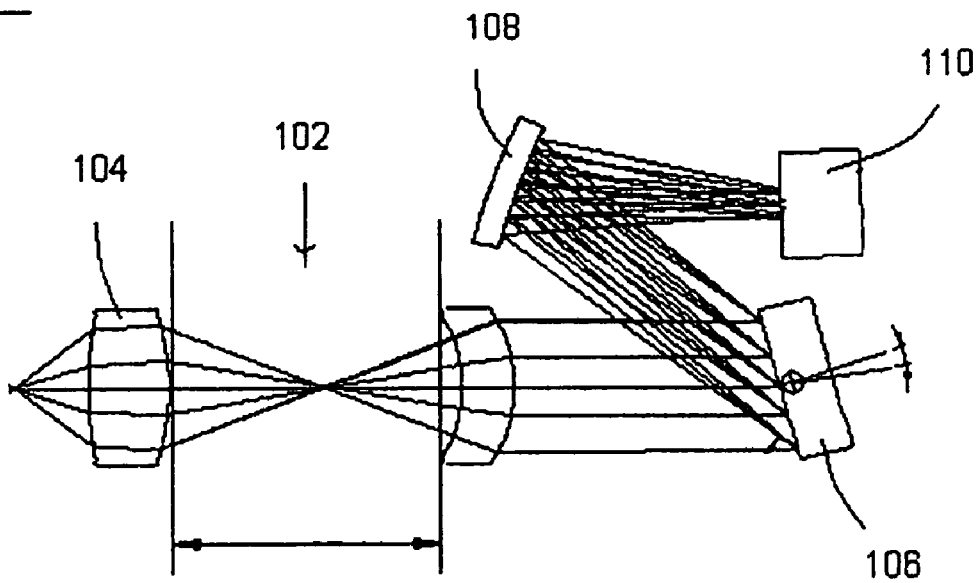
Figure 6C:
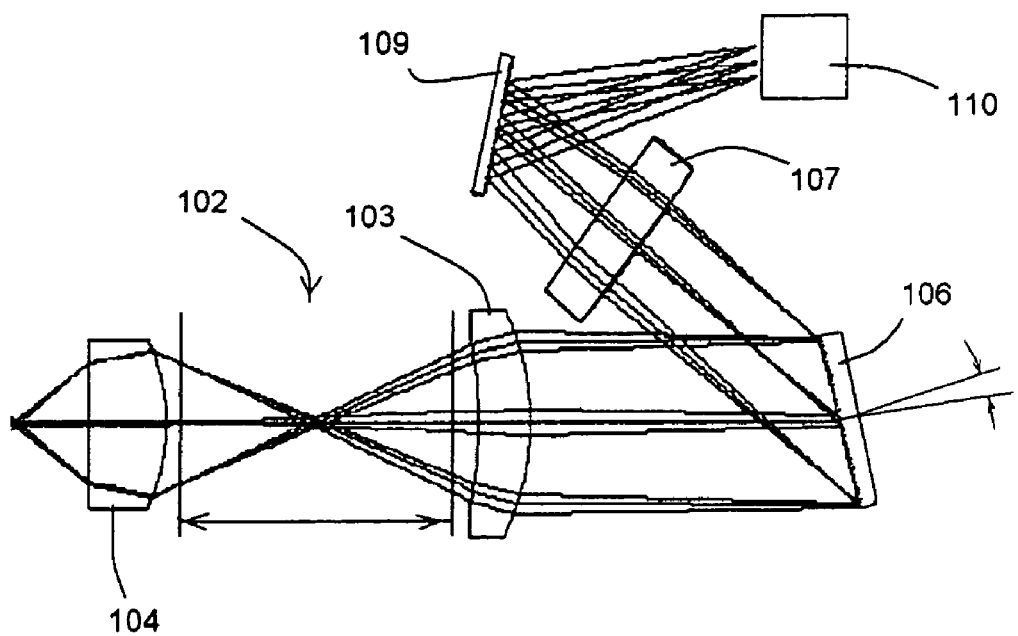
Figure 6D:
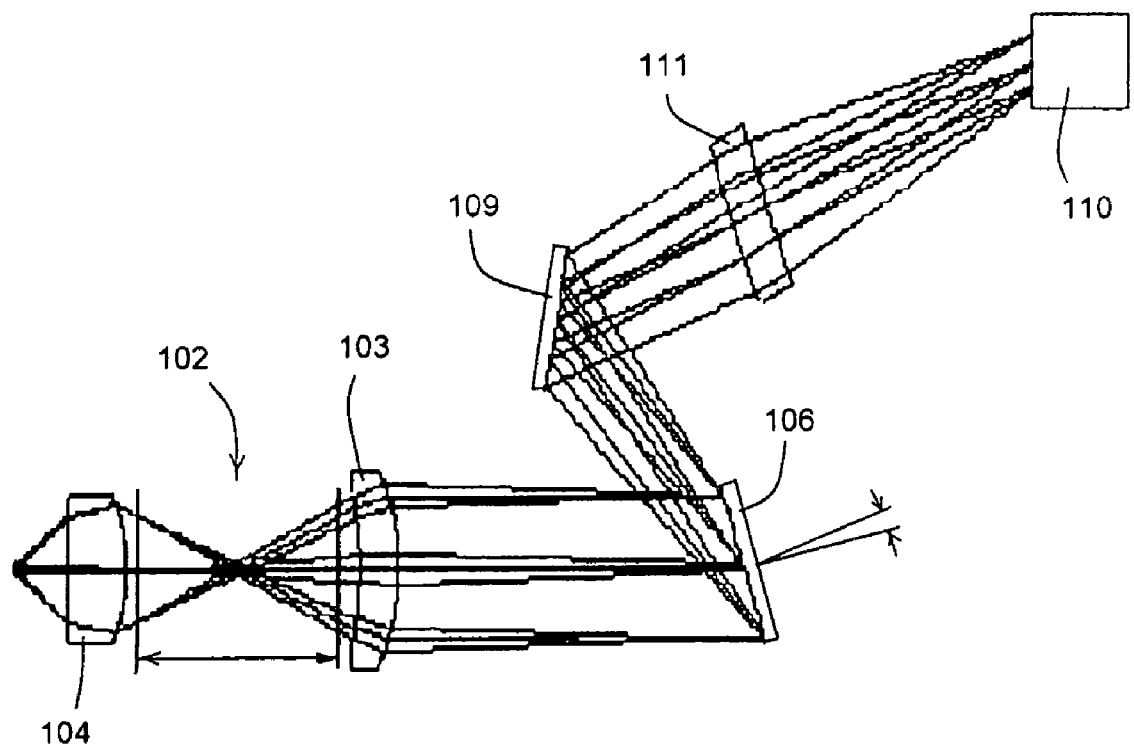

In FIGS. 6A and 6B, diffracted light from grating 106 is focused by an aspheric mirror 108 on to a sensor (detector) 110. By this technique, the source magnification is kept usably small, and the efficiency is high. The present invention contemplates that the lenses are coated with silicon, as it is the cheapest lens material with a reasonably good environmental stability for this wavelength range. In FIGS. 6C and 6D, a folding or turning mirror 109 is used in place of a concave focusing mirror 108.

FIGS. 6A-6D illustrate three alternative lens configurations. FIG. 6A illustrates an embodiment that uses a spherical lens 100 provided on one side of an adapter 102, which is also referred to as the sample cell. FIG. 6B illustrates the use of an aspheric lens 104 with adapter 102. FIG. 6C illustrates a focusing lens 107 provided before folding mirror 109. FIG. 6D illustrates a focusing lens 111 provided after folding mirror 109. The present invention also contemplates providing focusing lens before and after the folding mirror. The remaining components of the system, such as source, reflective grating 106, and detectors 110, can be configured in any of the arrangements contemplated by the present invention, including the specific examples discussed above.

The wavelengths of interest are about 8 to 9.5 microns for the agents, and 4 to 4.7 microns for $CO_2$ and $N_2O$, and with reference channels at 3.7 and 7.4 microns. The present invention contemplates that, the same optics and grating can scan both regions simultaneously, where the IR uses the grating first order, and the mid-IR uses the grating second order. A dichroic splitter is needed to separate the detectors.

The scanning rate for grating 106 is preferably in the 100 Hz to 300 Hz range. One hundred Hz is an approximate lower limit that is set by the required $CO_2$ bandwidth, i.e., 10 Hz. The upper limit is set by the IR detector response time, and mechanical constraints on the grating actuator. The spectrometer grating range of motion is about +/−5 degrees (mechanical) to cover the range including the reference channels, plus about 15% to 20% for turn-around. If the reference function is done some other way, or the grating spacing reduced, the range of motion may be cut to +/−3 degrees. In an exemplary embodiment of the present invention, the grating mirror is about 6 mm wide and 10 mm tall. These specs are well within an inexpensive state of the art at sinusoidal frequencies of 200 Hz-300 Hz range. A PbSe detector is used for the mid-IR because it is fast, sensitive, cheap, and familiar. The IR detector candidates are MercuryCadmiumTeluride (MCT), micro-thermopile, microbolometer, or pyroelectric.

The spectral data that will be collected by the MicroSpectrometer should include reference data on the noise floor (zero signal), source intensity (signal span, i.e., clear channel), and spectrum span calibration. Calibration can be done by reference to the $CO_2$ line and to an edge filter. Calibration in either band, or calibration between bands, is valid for both since the same scanner serves both. Signal zero and span need to be done on each separate sensor, so a clear channel and blocking function are required on each.

The present inventor recognized that in operation, the scanner that rotates the diffraction grating runs at a single frequency, and have a fixed scan angle. These requirements suggested to the present inventor that a resonant scanner would be an appropriate system for driving the diffraction grating. A resonant type of scanner drive system has several advantages: 1) the power requirements are minimized, assuming a high mechanical Q; 2) the motion of the scan tends to be an exact sinusoid with minimum harmonics; and 3) an accurate synchronizing signal can be derived from the drive circuit. A resonant scanner drive system does have a disadvantage in that the resonant frequency is dependent on the inertia (mass) of the whole moving system, and the magnitude of the restoring force (spring). If either change with time, temperature, or manufacturing variables, the resonant frequency will change.

The hurdles faced when attempting to use a resonant scanner drive system is to design a system where the inertial parts, other than the grating (which is fixed by the optical requirements), are minimized, air entrainment is minimized (to keep the mechanical Q high), and the overall size is minimized. Further, the system, as a whole must accept some variation in the resonance.

The present invention addresses these issued and provides a scanner drive system 200 as shown, for example, in FIGS. 7A-9. Scanner drive system 200 includes a taut band 202 that provides the rotational axis for a diffraction grating 204. It should be noted that the diffraction grating is omitted from FIG. 7A so that the features of the scanner drive system under the grating can be viewed. Band 202 also provides a spring return and a mechanical support for the moving components of the scanning system. Grating 204 is fastened on one side and generally at the center of band 202. A permanent magnet 206 is fastened on the other side of the band. Spacers 208 are provided on each side of band 202, so that as the assembly oscillates, the twisting band will not contact either grating 204 or magnet 206.

Band 202 is supported at its ends by a frame 210, which in an exemplary embodiment is square. During manufacture, the ends of band 202 are firmly attached to the frame while under tension. The present invention also contemplates holding frame 210 under compression during the process, so that the net tension in the band after attachment to the frame is predictable. The present invention contemplates attaching band 202 to frame 210 using a spot-weld, solder/braze, or glue if the attachment is re-enforced by bending the band over the outer edge of the frame.

In an exemplary embodiment, band 202 is 0.001" thick, 0.9 mm wide, and has a free length of about 7 mm. Grating substrate 204 is glass, 2 mm thick, and 6 mm in diameter. The resonant frequency is about 200 Hz, depending on the tension in the band, and the proximity of the drive pole-pieces to permanent magnet 206.

Permanent magnet 206 is advantageously a Neodymium-type, which provides an especially strong magnetic field for the size and mass. The magnet is mounted, as stated, on band 202 (with spacers 208) with the magnetic pole axis normal to the plane of the grating, i.e., the magnet surface that is attached to taut band is a pole. It may be either North or South, but a convention should be set during manufacture, because the phase of the oscillation relative to the driving pulse (see below) will be dependent on the polarity of the magnet.

The scanner is driven by the magnetic interaction between permanent magnet 206 and a proximate electro-magnet 212. Electro magnet 212, in an exemplary embodiment, has a "C" shaped core 214, with a winding 216 of suitable impedance wound around the center section of the "C". Electro-magnet 212 may be considered the stator of an AC motor and permanent magnet 206 may be considered as the rotor. Core 214 may be laminated iron, as in an audio transformer or ac motor, or it may be ferrite. A ferrite core is relatively lighter in weight, and provides somewhat less eddy-current losses, which in turn increases the mechanical Q of the system. Electro-magnet 212 is oriented such that a line between the two pole-pieces is perpendicular to the axis of the band 202. The spacing between magnet 206 and the electro-magnet pole-pieces is not especially critical, except that the clearance should not allow the magnet to contact a pole-piece under any reasonable excursion of the magnet. Otherwise, the magnet will stick to the pole-piece, and the system will stop.

The electrical drive provided to electro-magnet 212 is in the form of a short pulse. The scanner assembly will "ring" at the mechanical resonant frequency. Because the Q will be high (it is in the range of 100 to 150), it will take several pulses for the oscillation to reach amplitude equilibrium.

In a general oscillatory system, the drive will lag the motion by an amount approaching 90 degrees depending on the mechanical loss. The present system has very little loss, so the drive pulse, at resonance, will be at the maximum velocity point i.e., 90 degrees. The present system is both a motor and a generator, so any motion of the magnet will generate a return voltage in the electro-magnet coil.

Figure 9A:
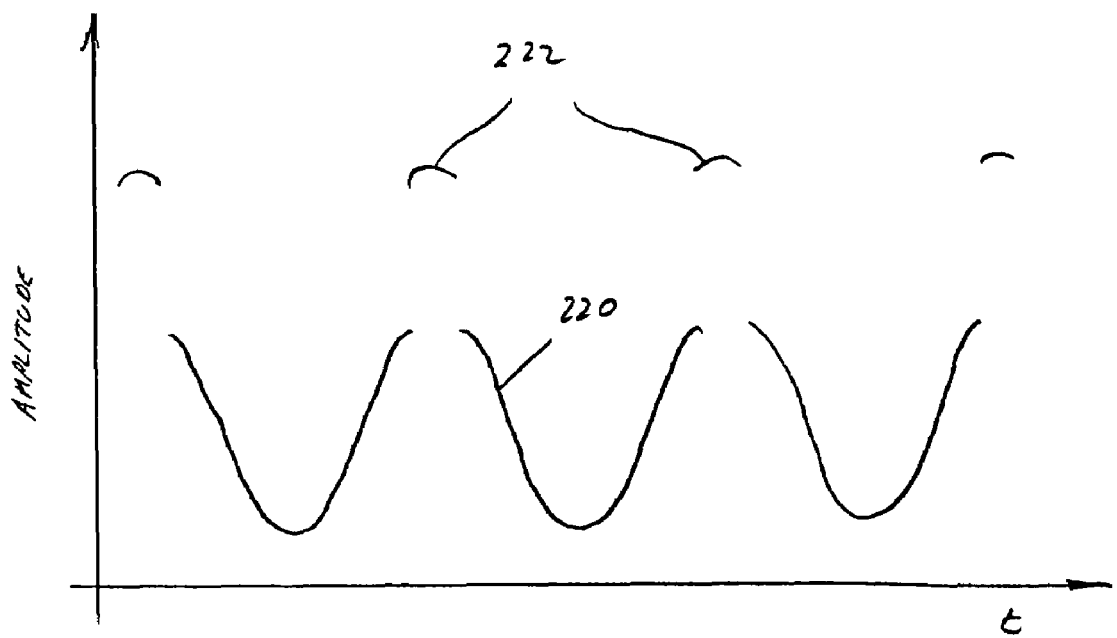
FIGS. 9A and 9B are waveforms showing the return signals for the scanner drive during resonance and an non-resonance, respectively.
Figure 9B:
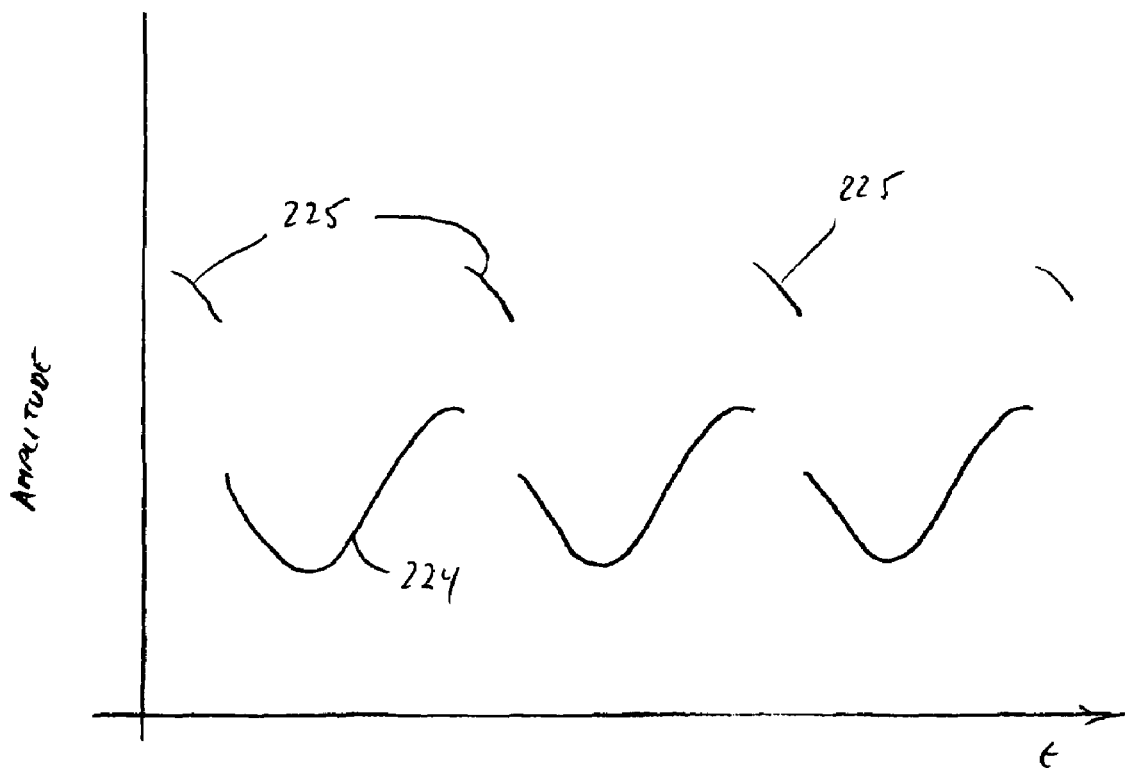

During resonance, the return signal can be shown or visualized as a sine wave 220, as shown in FIG. 9A. Sine wave 220 will in clued spikes 222 in the center of the sine wave are the drive pulse. Sine wave 220 is produced by attaching an oscilloscope directly to the drive coil, and a resistor was used to partially isolate the drive pulse electronics from the return signal. If the drive pulse rate is not at resonance, the reverse signal phase will be different from that shown in FIG. 9A. FIG. 9B illustrates a return signal 224 when the system is not at resonance. It can be appreciated that spikes 225 are not centered at the peak of the sine wave, but are offset or skewed from the center. By comparing the return signal just before the drive pulse to the signal just after the drive pulse, the phase error can be converted to a signal that can be used to adjust the drive frequency.

Figure 8:
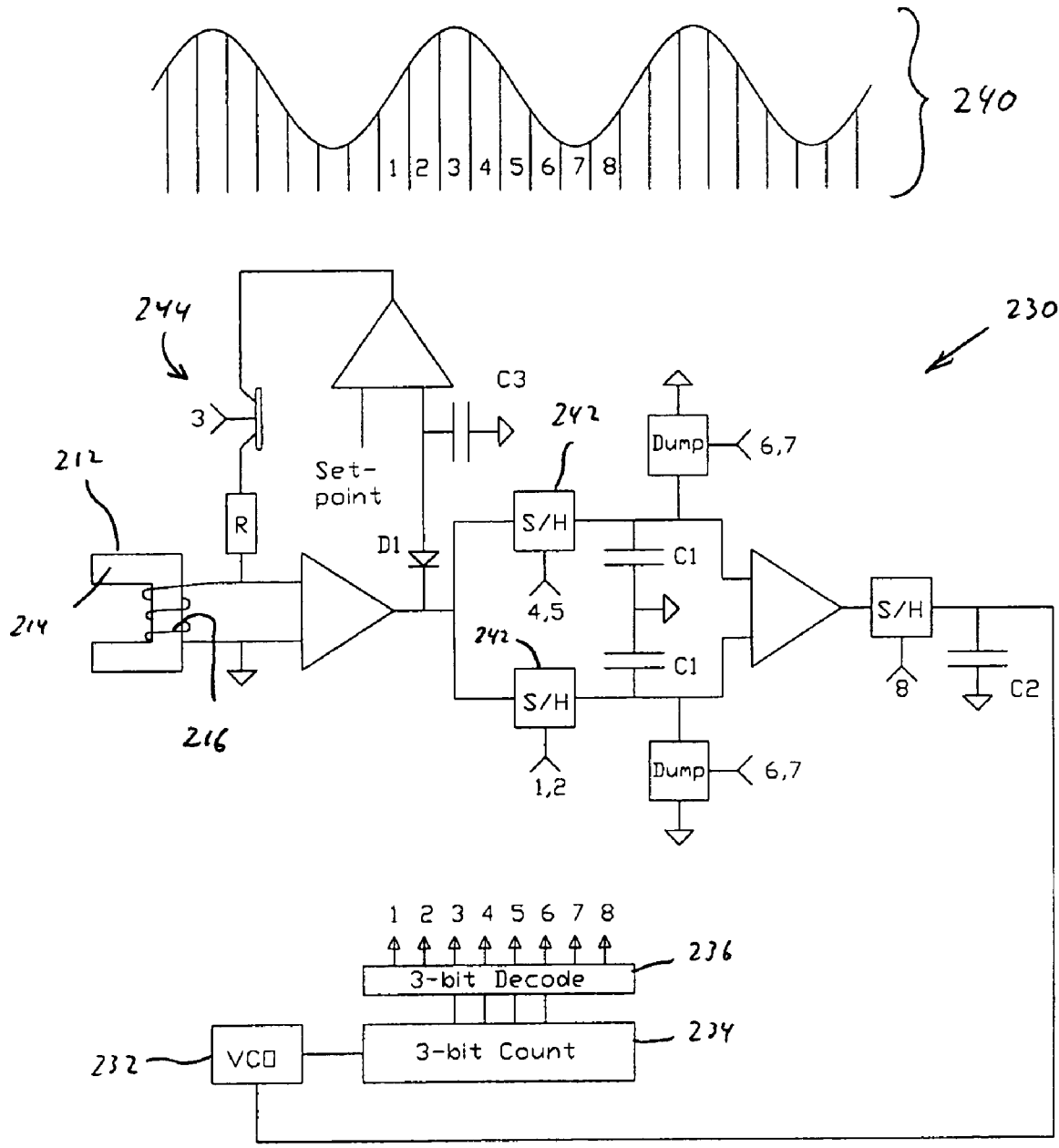
FIG. 8 is a schematic diagram of a circuit for performing an automatic scanning frequency adjustment according to the principles of the present invention.

A block schematic circuit 230 that will perform this automatic frequency adjustment is shown in FIG. 8. A voltage controlled oscillator (VCO) 232 provides the time-base for the system. It has a nominal frequency that is close to the mechanical resonance. Pulses from the VCO feed a 3-bit binary counter 234, which drives a 3-bit decode 236. The resulting 8 signals in time sequence are used to control the system.

In reference to the sine wave diagram 240 shown in FIG. 8, the first two time periods are used to collect data from the signal before the drive pulse, while the fourth and fifth periods collect data from the signal just after the pulse. The data are collected on capacitors C1 via sample and holds (S/H) 242. The drive pulse is generated in period three.

During periods six and seven, the signal differences, now in time sync, are transferred to capacitor C2, and to VCO 232. During period 8, the individual capacitors C1 are discharged to help slightly with loop response time. The time period 3 drives a transistor 244, such as a MOSFET, that injects current into drive coil 216 via an isolating resistor R.

The amplitude of the return signal is proportional to the peak velocity, which is proportional to the maximum scan angle, for a given frequency. Therefore, the return signal amplitude is used to provide feedback to the drive pulse size, thereby maintaining a constant scan angle. The negative half-cycle of the return signal is used for this purpose. Diode D1 and capacitor C3 provide a return signal average voltage to a differential amplifier. A fixed set-point is supplied to the other side of the amplifier. The amplified difference is the pulse amplitude.

The present invention also contemplates that the coil and pole structure can be rotated about an axis defined by the pole tips. In other words, the assembly can be folded back against the frame. Such a modification will make the scanner assembly shorter, but a little wider in one direction. The present invention also contemplates that two separate windings could be placed on the electro-magnet core. Two windings would provide a better impedance match for the driver and separately for the return amplifier. It would also improve the S/N in the return signal, because the signal would be floating.

Figure 7A:
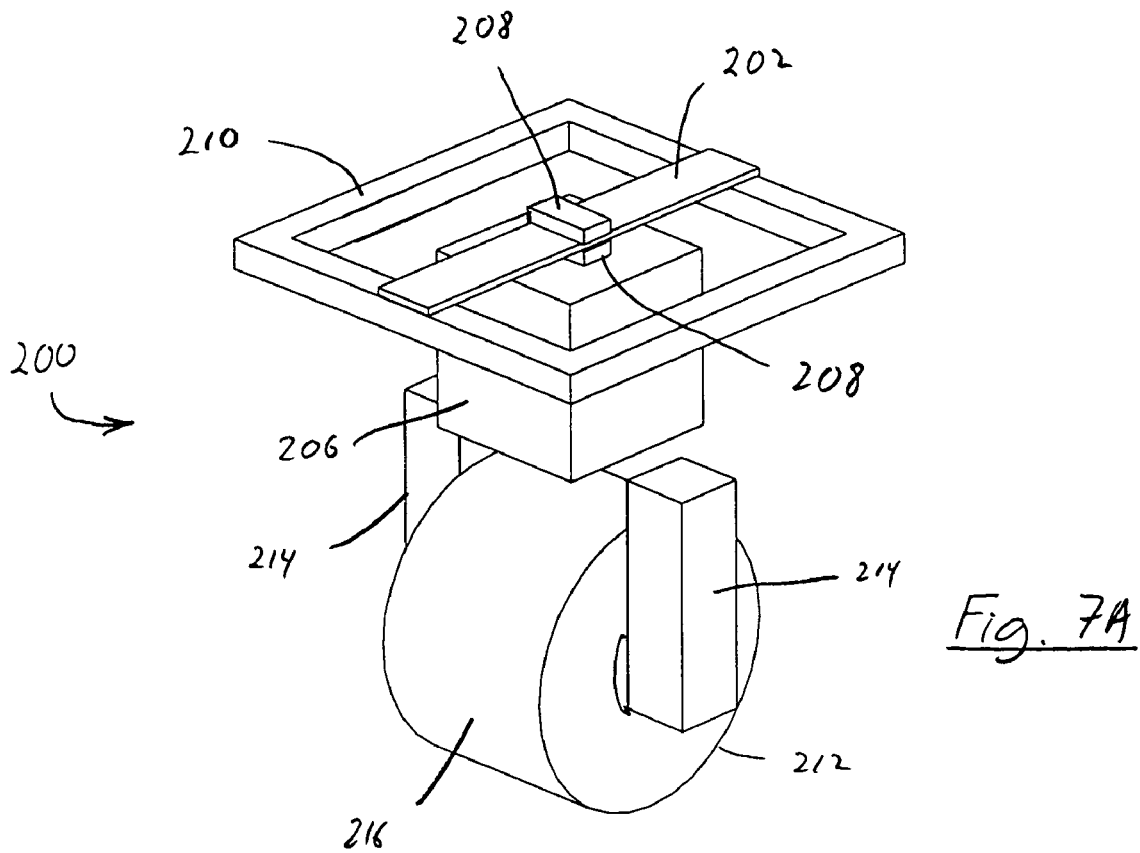
FIGS. 7A and 7B are top and bottom perspective views of an electro-mechanical scanner drive according to the principles of the present invention.
Figure 7B:
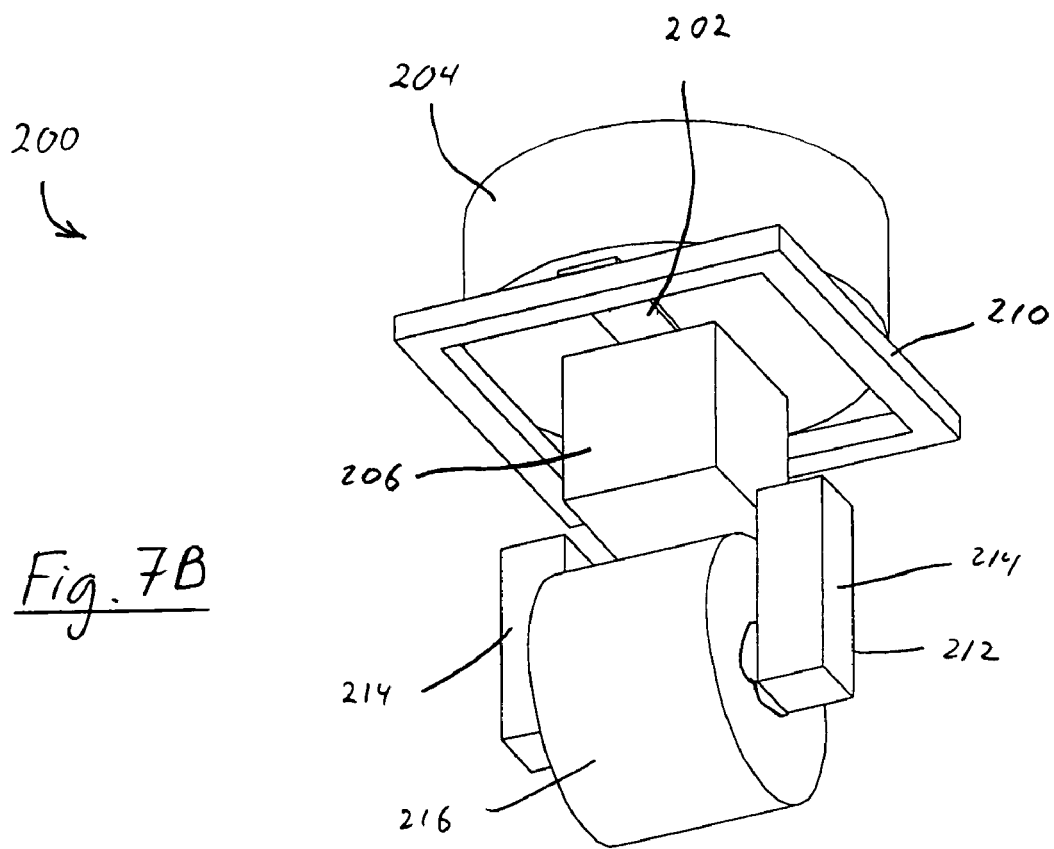

The grating is shown in FIG. 7B as a disk, but other shapes are contemplated, such as a square or rectangular. The important point is that the spectral resolution of a spectrometer is proportional, in part, to the width of the grating, i.e., the number of grating grooves that are in the light beam. In production, it would be advantageous to make the grating rotationally asymmetric, so that the grating grooves are more certain to be mounted parallel to the rotational axis, i.e., the long axis of the taut band.

The frame is expected to be the element that provides the primary strength for the scanner assembly, and, therefore, it would be the element that is fastened to the spectrometer system. The frame is shown as square. However, it could have other shapes, such as a circle, or some combination of shapes, and could include mounting bosses or brackets.

While the spectrometer of the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A spectrometer comprising:
   an infrared source for projecting an infrared beam;
   a gas sample cell positioned in the path of the infrared beam;
   a scanning mirror bearing a diffraction grating comprising a plurality of parallel lines and positioned in the path of the infrared beam after passage thereof through the gas sample cell such that the diffraction grating separates the infrared beam into a first order beam and a second order beam;
   a resonant scanner drive system adapted to oscillate the scanning mirror about an axis parallel to the diffraction grating lines;
   a splitter positioned in the path of the diffracted infrared beam from the scanning mirror and adapted to direct the first order beam along a first path and to direct the second order beam along a second path;
   a first focusing element positioned along the first path to focus the first order beam;
   a first detector positioned to receive the first order beam from the first focusing element;
   a first detector readout circuit operatively coupled to the first detector to receive a signal from the first detector;
   a second focusing element positioned along the second path to focus the second order beam;
   a second detector positioned to receive the second order beam from the second focusing element; and
   a second detector readout circuit operatively coupled to the second detector to receive a signal from the second detector.

2. The spectrometer of claim 1, wherein the splitter is a dichroic splitter for separating the diffracted infrared beam into discrete bands of interest.

3. The spectrometer of claim 1, wherein the first focusing element is a lens or a mirror, and the second focusing element is a lens or a mirror.

4. The spectrometer of claim 1, wherein the first focusing element is a lens or a mirror.

5. The spectrometer of claim 1, further comprising a lens disposed between the infrared source and the sample cell.

* * * * *